(12) United States Patent
Tortorici

(10) Patent No.: US 8,118,592 B2
(45) Date of Patent: Feb. 21, 2012

(54) HYBRID ORTHODONTIC APPLIANCE

(76) Inventor: Joseph Tortorici, Mount Sinai, NY (US)

( * ) Notice: Subject to any disclaimer, the term of this patent is extended or adjusted under 35 U.S.C. 154(b) by 449 days.

(21) Appl. No.: 12/048,734

(22) Filed: Mar. 14, 2008

(65) Prior Publication Data

US 2009/0130635 A1 May 21, 2009

Related U.S. Application Data

(60) Provisional application No. 60/989,617, filed on Nov. 21, 2007.

(51) Int. Cl.
*A61C 3/00* (2006.01)
(52) U.S. Cl. .............................. 433/6; 433/18
(58) Field of Classification Search ............. 433/2, 6–7, 433/18–19, 24; 128/848, 859–861
See application file for complete search history.

(56) References Cited

U.S. PATENT DOCUMENTS

| | | | | |
|---|---|---|---|---|
| 3,772,790 A * | 11/1973 | Swan-Gett et al. | ........... | 433/136 |
| 3,943,924 A * | 3/1976 | Kallestad et al. | ............. | 128/861 |
| 4,755,139 A * | 7/1988 | Abbatte et al. | .................... | 433/6 |
| 5,002,485 A * | 3/1991 | Aagesen | ........................... | 433/7 |
| 5,003,994 A * | 4/1991 | Cook | ............................. | 128/848 |
| 5,584,687 A * | 12/1996 | Sullivan et al. | .................... | 433/6 |
| 5,865,619 A * | 2/1999 | Cross et al. | ........................ | 433/6 |
| 5,975,893 A | 11/1999 | Chishti et al. | | |
| 6,302,686 B1 * | 10/2001 | Chott et al. | ........................ | 433/6 |
| 6,454,565 B2 | 9/2002 | Phan et al. | | |
| 6,553,996 B2 * | 4/2003 | Kittelsen et al. | .............. | 128/859 |
| 6,572,372 B1 | 6/2003 | Phan et al. | | |
| 6,581,604 B2 * | 6/2003 | Cook | ............................. | 128/859 |
| 6,675,806 B2 * | 1/2004 | Kittelsen et al. | .............. | 128/859 |
| 7,104,790 B2 | 9/2006 | Cronauer | | |
| 2003/0019497 A1 * | 1/2003 | Farrell | ......................... | 128/861 |
| 2003/0234022 A1 * | 12/2003 | Belfer | ............................ | 128/861 |
| 2007/0087300 A1 * | 4/2007 | Willison et al. | .................... | 433/6 |
| 2008/0066768 A1 * | 3/2008 | Dembro | ......................... | 128/861 |

* cited by examiner

*Primary Examiner* — Cris L Rodriguez
*Assistant Examiner* — Hao D Mai
(74) *Attorney, Agent, or Firm* — The Farrell Law Firm, P.C.

(57) ABSTRACT

An orthodontic appliance is provided for controlling positioning of a patient's teeth. The appliance includes at least one dental encasing component formed to overlay at least one of the patient's teeth and at least a portion of a palate of the patient. The at least one dental encasing component has a lingual surface and a labial surface. The appliance also includes at least one rigid component fused to an entire length of the lingual surface of the at least one dental encasing component and over a portion of the at least one dental encasing component overlaying a portion of the palate of the patient.

12 Claims, 6 Drawing Sheets

HYBRID ORTHODONTIC APPLIANCE

PRIORITY

This application claims priority under 35 U.S.C. §119(e) to a Provisional Patent Application filed in the USPTO on Nov. 21, 2007 and assigned Ser. No. 60/989,617, the disclosure of which is incorporated herein by reference.

BACKGROUND OF THE INVENTION

1. Field of the Invention

The present invention relates to orthodontic appliances, and more particularly, to hybrid orthodontic appliances with improved rigidity and structure for controlling the position of a patient's teeth.

2. Description of the Related Art

Removable orthodontic appliances are well known in the art for use before, during and after orthodontic treatment, for the purpose of moving and retaining the positions of an orthodontic patient's teeth. The appliances are removable and worn by patients in accordance with instructions from an orthodontist.

Removable orthodontic appliances may be constructed for use on both upper and lower dental arches and have typically been formed using variations of one of two methods.

A first method utilizes a combination of steel wire, springs, expansion screws and orthodontic acrylic. A wire framework for tooth alignment is placed along the labial and sometimes lingual areas of the dental arch. Orthodontic acrylic is applied to the palate to unite the wire frameworks and provide a secure foundation for controlled tooth-movement or retention. One common example of such an appliance is known as the Hawly retainer. This appliance has many functions and modifications due to its rigidity and structure. However, this appliance includes a wire that is visible across the front of a patient's teeth, which is adjusted periodically.

The second method utilizes thermal material. The thermal material is heated and then vacuum formed to a model of the patient's teeth. The invisible retainer encases the patient's teeth. This appliance is preferably transparent, but it lacks rigidity and structure, and is thereby flexible and easily cracked and broken. Invisible orthodontic appliances have been utilized in the orthodontic industry for at least the last 25 years. The primary function of the invisible retainer is to retain the position of the teeth following orthodontic treatment, or to allow for minor tooth movement using a series of these retainers.

A need exists for an appliance that combines the advantages of the two previous techniques, while at the same time eliminating the disadvantages of both.

SUMMARY OF THE INVENTION

The present invention has been made to address at least the above problems and/or disadvantages and to provide at least the advantages described below. Accordingly, an aspect of the present invention provides an orthodontic appliance that controls positioning of a patient's teeth.

Another aspect of the present invention provides a method for making an orthodontic appliance that controls positioning of a patient's teeth.

According to one aspect of the present invention, an orthodontic appliance is provided that controls positioning of a patient's teeth. The appliance includes at least one dental encasing component formed to overlay at least one of the patient's teeth and at least a portion of a palate of the patient. The at least one dental encasing component has a lingual surface and a labial surface. The appliance also includes at least one rigid component fused to an entire length of the lingual surface of the at least one dental encasing component and over a portion of the at least one dental encasing component overlaying at least a portion of the palate of the patient.

According to another aspect of the present invention, a method of making an orthodontic appliance that controls positioning of a patient's teeth is provided. A model of at least a portion of at least one dental arch and at least a portion of a palate of the patient is formed. A thermal material is formed over at least a portion of the model to overlay at least one of the patient's teeth and at least a portion of a palate of the patient to form at least one dental encasing component having a lingual surface and a labial surface. An acrylic material is applied to an entire length of the lingual surface of the at least one dental encasing component and over a portion of the least one dental encasing component overlaying a portion of the palate of the model to form at least one rigid component.

BRIEF DESCRIPTION OF THE DRAWINGS

Aspects, features and advantages of the present invention will become more apparent from the following detailed description when taken in conjunction with the accompanying drawings in which.

DETAILED DESCRIPTION OF THE PREFERRED EMBODIMENTS

Figure 1:
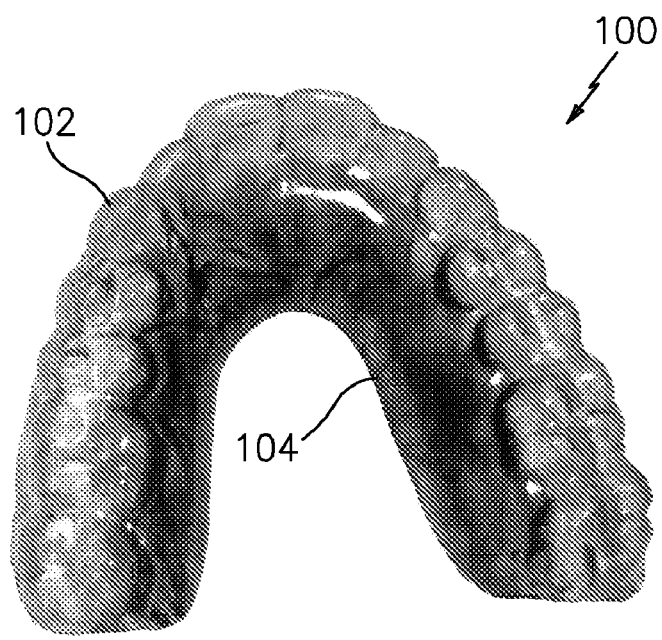
FIG. 1 is a diagram illustrating a hybrid retaining orthodontic appliance, according to an embodiment of the present invention.

Preferred embodiments of the present invention are described in detail with reference to the accompanying drawings. In the drawings, the same or similar elements are denoted by the same or similar reference numerals even though they are depicted in different drawings. Detailed descriptions of constructions or processes known in the art may be omitted to avoid obscuring the subject matter of the present invention.

Referring initially to FIG. 1, a diagram illustrates a hybrid retaining orthodontic appliance, according to an embodiment of the present invention. A hybrid retaining orthodontic appliance 100 for use on a patient's maxillary (upper) dental arch is illustrated, however appliances may be suited for both maxillary and mandibular (lower) arches. Hybrid retaining orthodontic appliance 100 has a dental encasing component 102 specifically shaped to overlay the teeth and a portion of the palate of the patient. In order to encase the teeth of the patient, dental encasing component 102 has a lingual surface formed to overlay the interior side of the teeth of the patient, and a labial (and buckle) surface formed to overlay the exterior side of the teeth of the patient. Dental encasing component 102 is fused with a rigid component 104 at the lingual surface of hybrid retaining orthodontic appliance 100. Rigid component 104 is joined around the entire length of the lingual surface of dental encasing component 102 and is formed over a portion of dental encasing component 102 that overlays a portion of the palate of the patient.

In a specific embodiment of the present invention, dental encasing component 102 is formed of at least substantially transparent thermoplastic material so that hybrid retaining orthodontic appliance 100 is not noticeable when worn by the patient, and is preferably substantially invisible. In alternative embodiments, dental encasing component 102 may be formed of any material capable of overlaying the teeth of the patient, and also may be provided in a variety of colors. Further, dental encasing component 102 of FIG. 1 is formed to encase a full dental arch of the patient. However, the number of teeth encased by dental encasing component 102 is dependent upon the specific treatment of the patient. Rigid component 104 is preferably acrylic and also may be provided in a variety of colors. Rigid component 104 provides structure and rigidity to dental encasing component 102, thereby making the preferred embodiment of hybrid retaining orthodontic appliance 100 both rigid and substantially invisible when worn.

Figure 2:
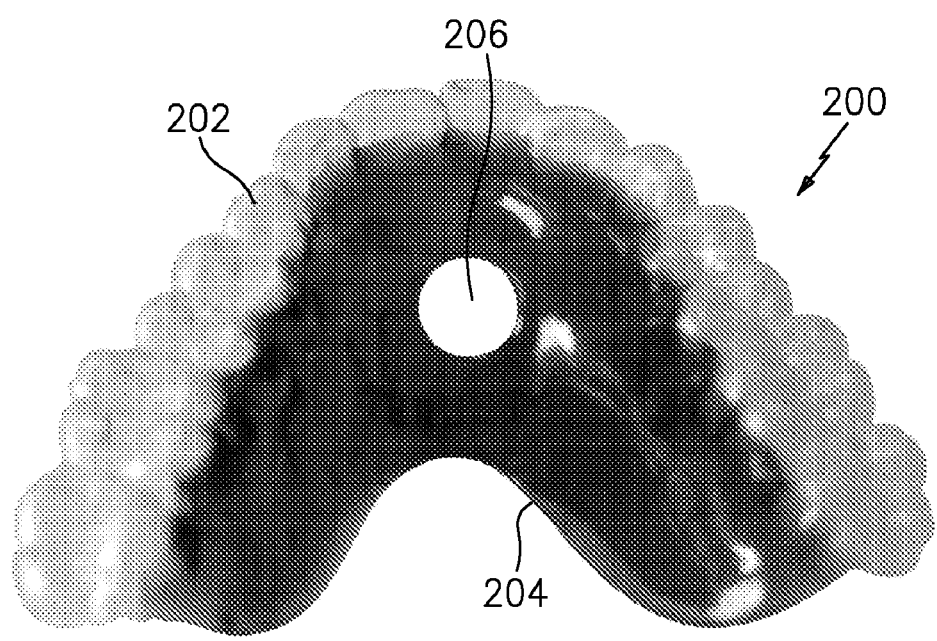
FIG. 2 is a diagram illustrating a hybrid retaining orthodontic appliance, according to another embodiment of the present invention.

Referring now to FIG. 2, a diagram illustrates a hybrid retaining orthodontic appliance, according to another embodiment of the present invention. A hybrid retaining orthodontic appliance 200 for use on a patient's upper dental arch is illustrated. Hybrid retaining orthodontic appliance 200 has a dental encasing component 202 fused to a rigid component 204 in a manner similar to that of FIG. 1. In this embodiment, an aperture 206 is provided through both dental encasing component 202 and rigid component 204 in an area overlaying the palate of the patient, in order to provide a thrusting appliance with a resting area for the tongue.

Figure 3:
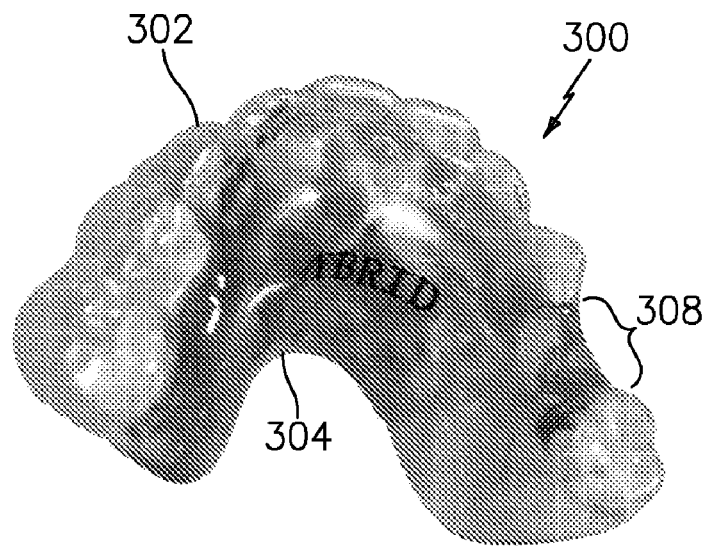
FIG. 3 is a diagram illustrating a hybrid space maintaining orthodontic appliance, according to an embodiment of the present invention.

Referring now to FIG. 3, a diagram illustrates a hybrid space maintaining orthodontic appliance, according to an embodiment of the present invention. A hybrid space maintaining orthodontic appliance 300 for use on a patient's upper dental arch is illustrated. Hybrid space maintaining orthodontic appliance 300 has a dental encasing component 302 fused to a rigid component 304 in a manner similar to that of FIG. 1. Dental encasing component 302 may overlay a majority of the patient's teeth, as well as a space between teeth of the patient in the patient's dental arch. Rigid component 304 is formed to extend from the palate of the patient, outward between teeth of the patient, so that it also overlays the space between the teeth of the patient. Rigid component 304 assists in maintaining a space 308 between two teeth of the patient when hybrid space maintaining orthodontic appliance 300 is worn by the patient by providing rigidity between the teeth of the patient. Space 308 may be positioned between any two teeth, or between multiple sets of teeth, depending on the treatment of the patient.

Figure 4:
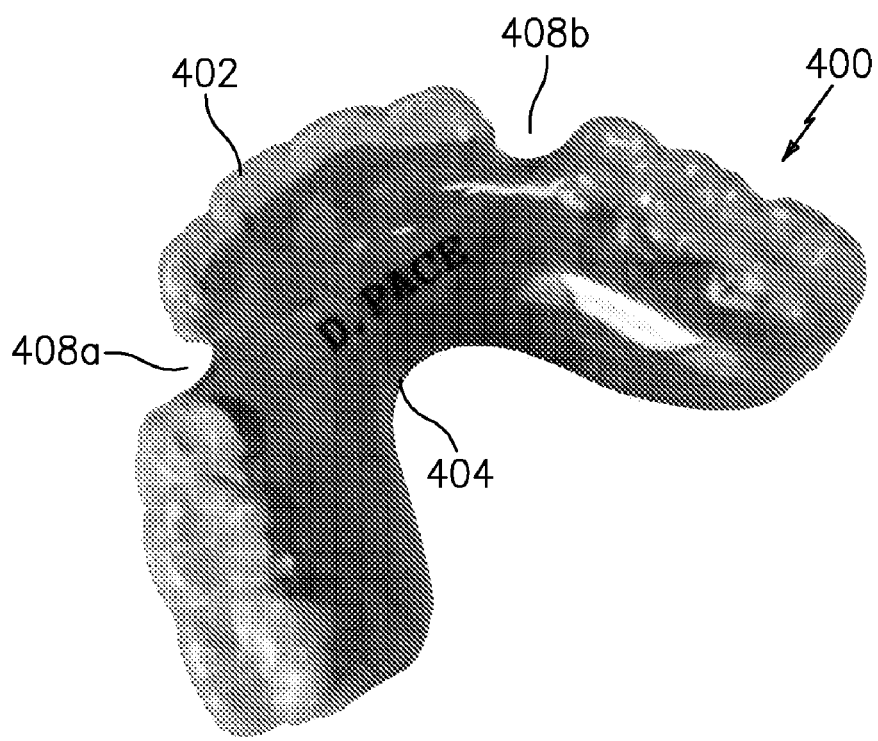
FIG. 4 is a diagram illustrating a hybrid space maintaining orthodontic appliance, according to another embodiment of the present invention.

Referring now to FIG. 4, a diagram illustrates another hybrid space maintaining orthodontic appliance, according to an embodiment of the present invention. A hybrid space maintaining orthodontic appliance 400 for use on a patient's upper dental arch is illustrated. Hybrid space maintaining orthodontic appliance 400 has a dental encasing component 402 fused to a rigid component 404 in a manner similar to that of FIG. 1. Dental encasing component 402 may overlay a majority of the patient's teeth, but does not overlay spaces 408a, 408b between the teeth. These spaces may be left open so that new teeth have the ability to erupt into spaces maintained by hybrid space maintaining device 400, without being inhibited by hybrid space maintaining device 400. Spaces 408a, 408b may be positioned between any two teeth, or between multiple sets of teeth, depending on the treatment of the patient.

Figure 5:
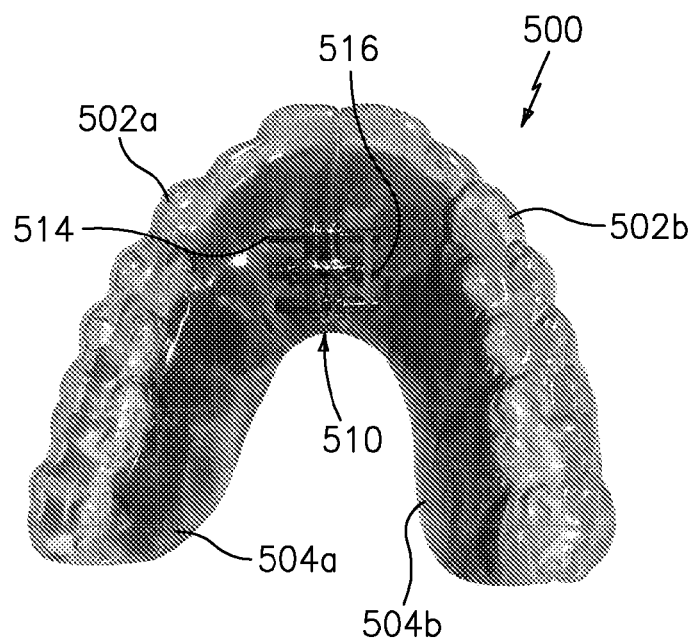
FIG. 5 is a diagram illustrating a hybrid palate expanding orthodontic appliance, according to an embodiment of the present invention.

Referring now to FIG. 5, a diagram illustrates a hybrid palate expanding orthodontic appliance, according to an embodiment of the present invention. Hybrid palate expanding orthodontic appliance 500 is divided into two segments, each segment having a dental encasing component 502a, 502b fused to a respective rigid component 504a, 504b, in a manner similar to that of FIG. 1. As also shown in FIG. 1, dental encasing components 502a, 502b are formed to overlay a full dental arch of the patient, however, the number of teeth encased and portion of the palate overlayed may vary depending on the specific treatment of the patient.

An expansion device 510 joins the two segments of hybrid palate expanding orthodontic appliance 500 at a central location of the palate, and maintains the rigidity of hybrid palate expanding orthodontic appliance 500. Interconnecting elements of expansion device 510 are disposed in both rigid components 504a, 504b at a connection point in this central location. Examples of such expansion devices that are commonly used in the field of orthodontics include products of Dentaurum, of Ispringen, Germany. Expansion device 510 has two guide rods 514 between which is disposed a threaded bar 516 having pinholes. A wire key may be inserted into a pinhole, and when the wire key is turned, the distance between the two segments of hybrid retaining appliance 500 is increased, thereby expanding the palate. For example, each quarter turn of the wire key may expand the palate by 0.25 millimeter (mm). The position of expansion device 510 in rigid components 504a, 504b and the division of the appliance is dependent upon the specific treatment of the patient.

Figure 6:
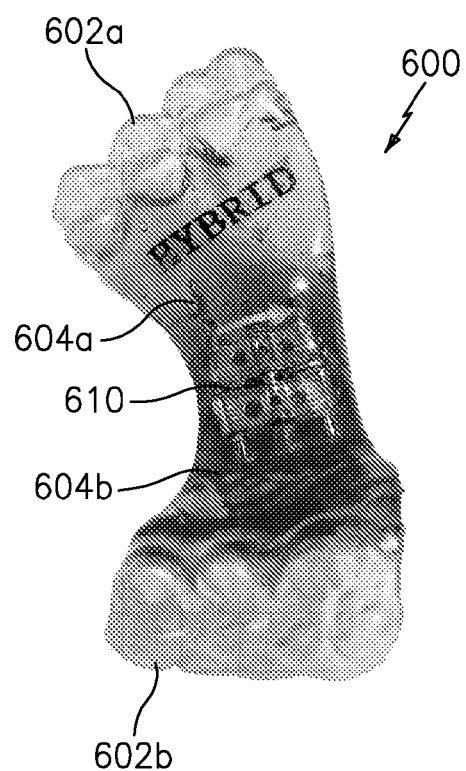
FIG. 6 is a diagram illustrating a hybrid palate expanding orthodontic appliance, according to another embodiment of the present invention.

Referring now to FIG. 6 a diagram illustrates a hybrid palate expanding orthodontic appliance, according to another embodiment of the present invention. A hybrid palate expanding orthodontic appliance 600 has two segments, with a dental encasing component 602a, 602b fused to a respective rigid component 604a, 604b. An expansion device 610 joins the two segments and may contain similar components to those described above with respect to FIG. 5. Expansion device 610 is disposed in a central portion of the palate where rigid components 604a, 604b meet. Thus, expansion device 610 is disposed such that it may expand the palate of the patient. In this embodiment, dental encasing components 602a, 602b each overlay a few teeth of the patient on opposing sides of the patients mouth, and rigid components 604a, 604b extend across the palate of the patient providing a bridge across the palate between dental encasing components 602a, 602b.

Figure 7:
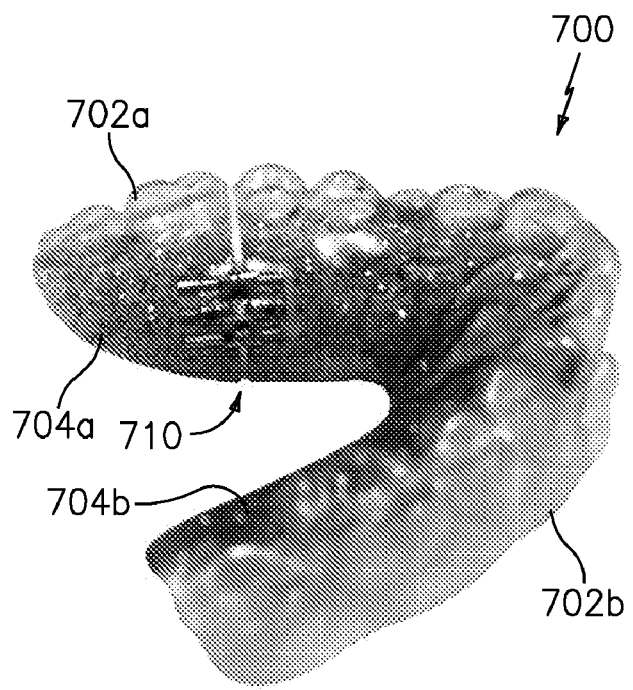
FIG. 7 is a diagram illustrating a hybrid distalizing orthodontic appliance, according to an embodiment of the present invention.

Referring now to FIG. 7, a diagram illustrates a hybrid distalizing orthodontic appliance, according to an embodiment of the present invention. A hybrid distalizing orthodontic appliance 700 has two dental encasing components 702a, 702b fused to respective rigid components 704a, 704b, which are joined by an expansion device 710. Dental encasing components 702a, 702b, and respective rigid components 704a, 704b meet where expansion between two teeth is desired. Expansion device 710 is disposed in portions of rigid components 704a, 704b formed closest to the lingual surface of the dental encasing components 702a, 702b, such that it may expand the space between two teeth of the patient.

Expansion device 710 may be positioned between any two teeth of the patient. This position and the division of the appliance are dependent upon the specific treatment of the patient. The appliance is also capable of housing multiple expansion devices disposed between different sets of teeth. Further, an appliance is capable of housing expansion devices utilized for both distalization and palate expansion, with multiple appliance divisions.

Figure 8:
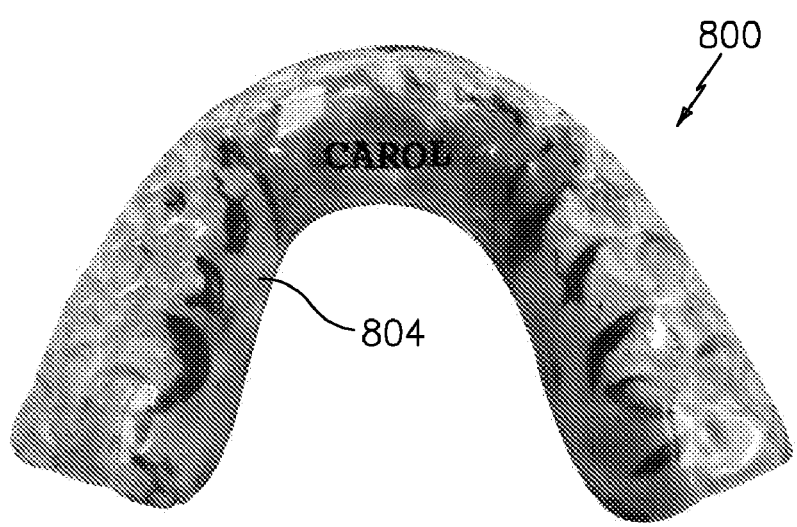
FIG. 8 is a diagram illustrating a hybrid Temporo-Mandibular Joint (TMJ) orthodontic appliance, according to another embodiment of the present invention.

Referring now to FIG. 8, a diagram illustrates a hybrid TMJ orthodontic appliance, according to another embodiment of the present invention. A hybrid TMJ orthodontic appliance 800 for use on a patient's upper dental arch is illustrated. Hybrid TMJ orthodontic appliance 800 has a rigid component 804 fused over an entire surface of dental encasing component. Because rigid component 804 is fused over the entire surface, the portion of rigid component 804 that extends over the teeth of the patient may be substantially clear, thereby still enabling the substantial invisibility of the appliance. This appliance opens the bite of the patient, and separates the opposing arches of the patient, thereby relieving TMJ and bruxism discomfort.

Figure 9:
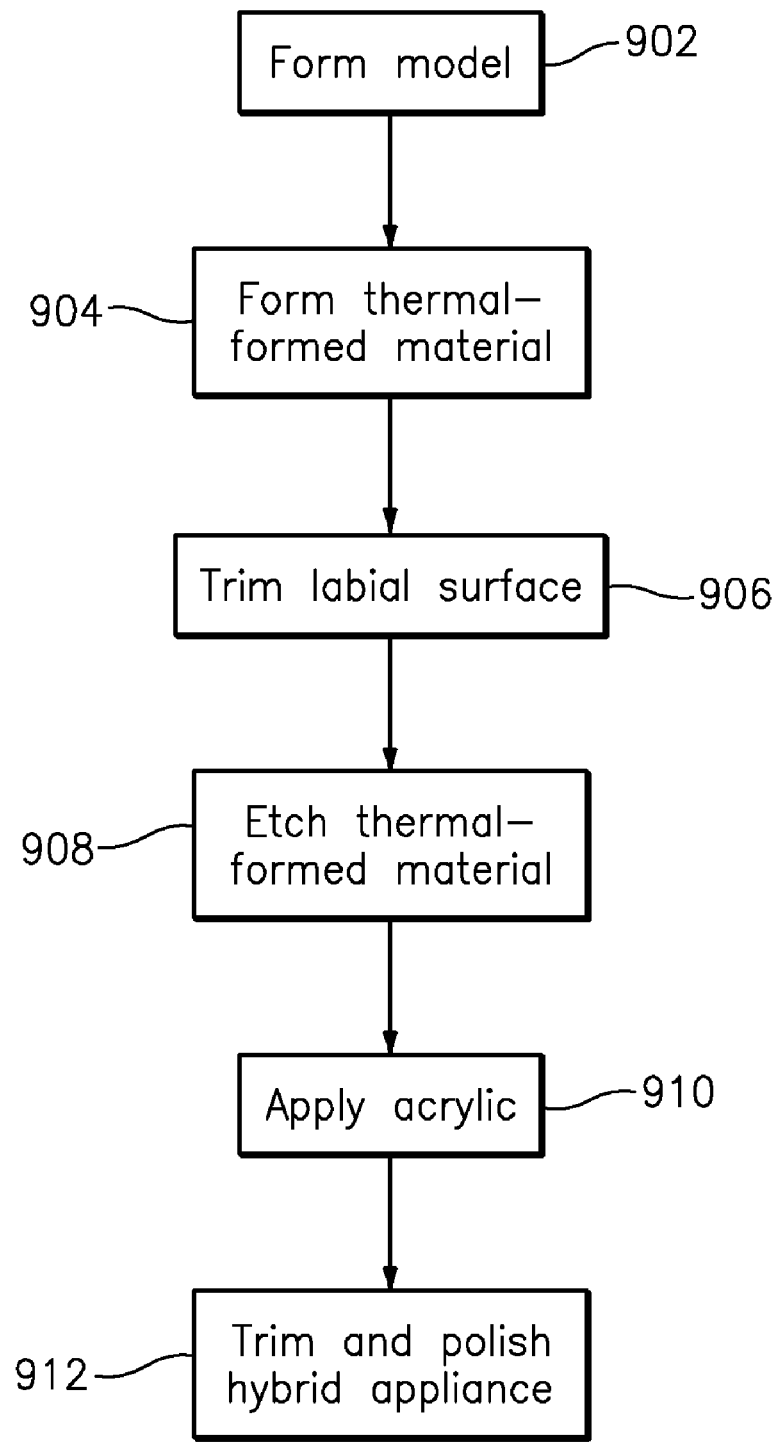
FIG. 9 is a flow diagram illustrating a hybrid orthodontic appliance creation methodology, according to an embodiment of the present invention.

Referring now to FIG. 9, a flow diagram illustrates a hybrid orthodontic appliance creation methodology, according to an embodiment of the present invention. The methodology begins in block 902 in which a model is formed from a patient's upper or lower dental arch. While forming the model, as much palate or soft tissue is included in the model as possible. In block 904, a thermal-formed material is formed over the model. This process is achieved using a thermal forming vacuum machine. Examples of such thermal-formed materials commonly used in the field of orthodontics include products of Raintree Essix, of Metairie, La. In block 906, after the thermal-formed material cools, a labial surface is trimmed, leaving a reasonable amount of material on the palate. In block 908, the thermal-formed material may optionally be etched along the palate. Etching may be performed with, for example, Great Lakes Orthodontic Monomer. In block 910, an acrylic is applied to the thermal-formed material along an entire length of a lingual surface and covering at least a portion of the palate. The acrylic is then processed, preferably with the use of a pressure pot, which allows air bubbles to release. In block 912, the hybrid orthodontic appliance is trimmed and polished, terminating the methodology.

Figure 10:
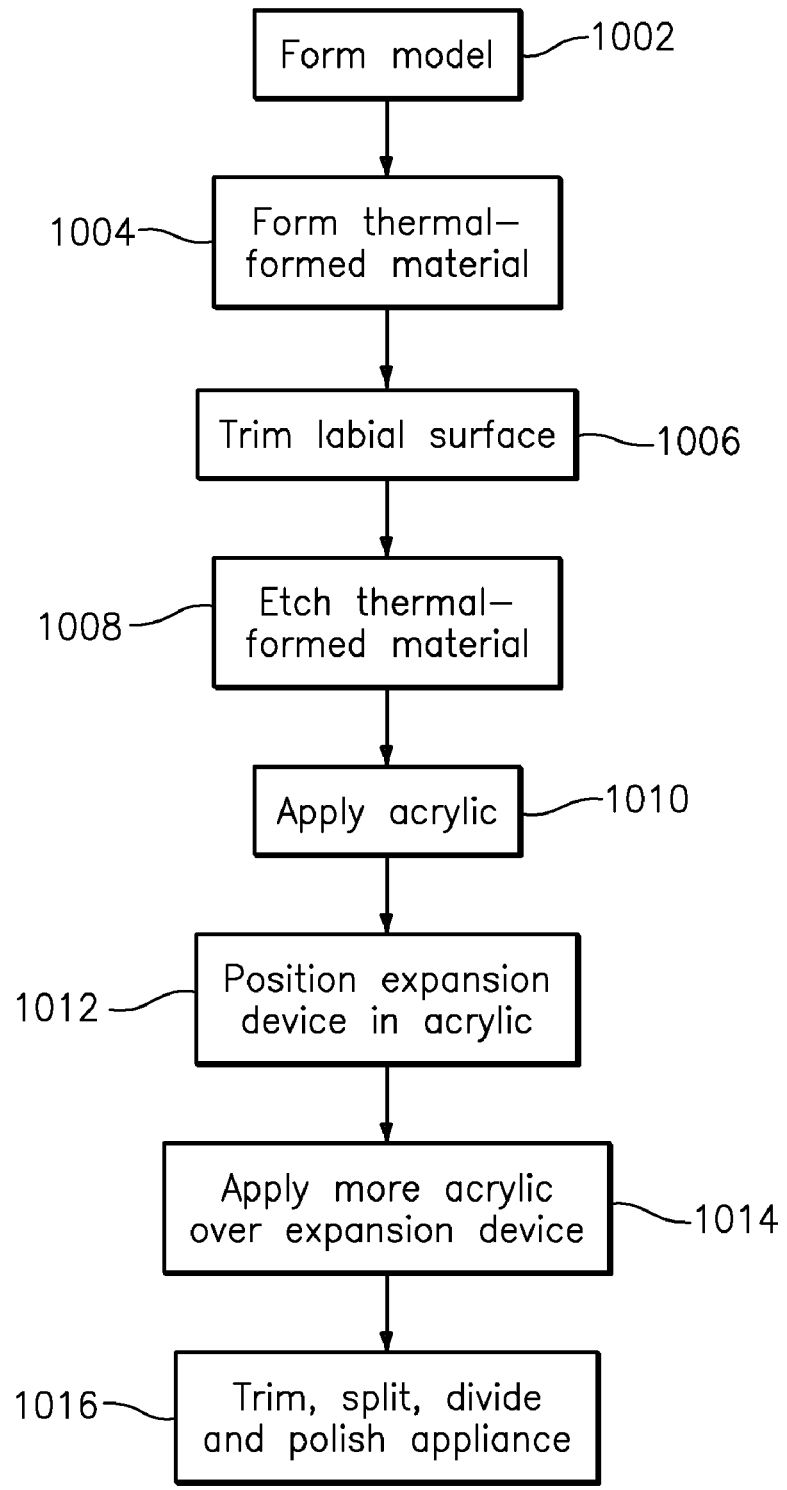
FIG. 10 is a flow diagram illustrating a hybrid expanding orthodontic appliance creation methodology, according to an embodiment of the present invention.

Referring now to FIG. 10, a flow diagram illustrates a hybrid expanding orthodontic appliance creation methodology, according to an embodiment of the present invention. The methodology begins in block 1002 where a model is formed from a patient's upper or lower dental arch in a similar manner to that described in FIG. 9. In block 1004, thermal-formed material is formed over the model. This process is achieved using a thermal forming vacuum machine. In block 1006, after the thermal-formed material cools, a labial surface is trimmed, leaving a reasonable amount of material on the palate. In block 1008, the thermal-formed material is optionally etched along the palate. In block 1010, acrylic is applied to the thermal-formed material along an entire length of a lingual surface and covering at least a portion of the palate.

In block 1012, an expansion device is positioned in the acrylic. The expansion device is positioned in accordance with the treatment of the patient. For example, an expansion device may be positioned in the center of the palate so that the appliance may function as a palate expander. The expansion device may also be positioned close to the lingual surface so that the appliance may act as a distalizer. Multiple expansion devices may be positioned in the appliance to achieve, for example, distalization of multiple teeth or both distalization and palate expansion.

In block 1014, additional acrylic is applied over the expansion device. The acrylic is then processed in a manner similar to that of Claim 9. In block 1016, the hybrid expanding orthodontic appliance is trimmed, split, divided and polished. The hybrid expanding orthodontic appliance is divided so that multiple portions of the device are joined by the expansion device. More specifically, the appliance is divided in accordance with the type of expansion screw as well as the number of expansion devices.

The resulting appliance includes a covered occlusion without stainless steel wires that provides improved aesthetics over conventional Hawley appliances and improved rigidity over conventional invisible retaining appliances. The appliance may be utilized as a platform for all orthodontic appliances such as those appliances described in FIGS. 1-8, as well as multi-expansion appliances, space maintainer appliances, thrusting appliances, thumb sucking appliances, TMJ appliances, bruxism appliances, bite plate appliances, spring retainer appliances, snoring appliances, and minor tooth repositioning appliances.

While the invention has been shown and described with reference to a certain preferred embodiment thereof, it will be understood by those skilled in the art that various changes in form and details may be made therein without departing from the spirit and scope of the invention.

What is claimed is:

1. An orthodontic appliance that controls positioning of a patient's teeth comprising:
    at least one thermoplastic dental encasing component formed to overlay at least one of the patient's teeth and at least a portion of a palate of the patient, the at least one dental encasing component having a lingual surface and a labial surface; and
    at least one rigid acrylic, component fused to the at least one thermoplastic dental encasing component and extending from an entire length of the lingual surface of the at least one thermoplastic dental encasing component in a direction toward the palate of the patient and completely covering the at least a portion of the palate of the patient;
    wherein only the at least one thermoplastic dental encasing component fully overlays the at least one of the patient's teeth and all portions of the palate overlayed by the at least one thermoplastic dental encasing component are also overlayed by the at least one rigid acrylic component, wherein the at least one rigid acrylic component has a higher rigidity than the at least one thermoplastic dental encasing component, and wherein the at least one rigid acrylic component increases a rigidity of an entire arch defined by the at least one thermoplastic dental encasing component without fully overlaying the at least one of the patient's teeth in order to control positioning of the patient's teeth.

2. The orthodontic appliance of claim 1, wherein the at least one thermoplastic dental encasing component is substantially transparent.

3. The orthodontic appliance of claim 1, wherein the at least one thermoplastic dental encasing component is formed to overlay a full dental arch of the patient.

4. The orthodontic appliance of claim 1, wherein the at least one thermoplastic dental encasing component has a labial surface only where it overlays the at least one of the patient's teeth.

5. The orthodontic appliance of claim 1, wherein the at least one thermoplastic dental encasing component and the at least one rigid acrylic component comprise an aperture disposed over the palate of the patient.

6. The orthodontic appliance of claim 1, wherein the at least one thermoplastic dental encasing component overlays a space between two teeth of the patient and the at least one rigid acrylic component extends outward from the lingual surface of the dental encasing component over the space between the two teeth of the patient to the labial surface of the at least one thermoplastic dental encasing component.

7. The orthodontic appliance of claim 1, wherein the at least one thermoplastic dental encasing component comprises two thermoplastic dental encasing components and the at least one rigid acrylic component comprises two rigid acrylic components, and wherein each of the two rigid acrylic components is fused to the entire length of the lingual surface of a respective one of the two thermoplastic dental encasing components.

8. The orthodontic appliance of claim 7, wherein the two rigid acrylic components are joined by an expansion device.

9. The orthodontic appliance of claim 8, wherein a first interconnecting element of the expansion device is at least partially encased in one of the two rigid acrylic components and a second interconnecting element of the expansion device is at least partially encased in another of the two rigid acrylic components.

10. The orthodontic appliance of claim 8, wherein the expansion device comprises guide rods and a threaded bar between the guide rods, each at least partially encased in at least one of the two rigid acrylic components.

11. The orthodontic appliance of claim 8, wherein the expansion device is disposed in portions of the two rigid acrylic components formed to overlay a center of the palate of the patient.

12. The orthodontic appliance of claim 8, wherein the expansion device is disposed in portions of the two rigid acrylic components closest to the lingual surfaces of the two thermoplastic dental encasing components.

\* \* \* \* \*